United States Patent

Chasan

[11] Patent Number: 5,988,174
[45] Date of Patent: Nov. 23, 1999

[54] METHOD FOR COLORING THE SKIN

[75] Inventor: Paul E. Chasan, San Diego, Calif.

[73] Assignee: University of Utah, Salt Lake City, Utah

[21] Appl. No.: 08/898,065

[22] Filed: Jul. 22, 1997

Related U.S. Application Data

[60] Division of application No. 08/504,438, Jul. 20, 1995, Pat. No. 5,713,890, which is a continuation-in-part of application No. 08/278,021, Jul. 20, 1994, Pat. No. 5,496,304.

[51] Int. Cl.⁶ .................................................. A61B 17/00
[52] U.S. Cl. .............................. 128/898; 606/1; 606/116; 606/186
[58] Field of Search ................................. 128/898; 606/1, 606/116, 185, 186; 604/46–48; 81/9.22

[56] References Cited

U.S. PATENT DOCUMENTS

| | | |
|---|---|---|
| 1,699,012 | 1/1929 | Naylor . |
| 4,392,498 | 7/1983 | Niemeijer . |
| 4,437,361 | 3/1984 | Steckel et al. . |
| 4,488,550 | 12/1984 | Niemeijer . |
| 4,608,045 | 8/1986 | Fretwell . |
| 4,671,277 | 6/1987 | Beuchat . |
| 4,796,624 | 1/1989 | Trott et al. . |
| 4,798,582 | 1/1989 | Sarath et al. . |
| 5,139,029 | 8/1992 | Fishman et al. . |
| 5,279,552 | 1/1994 | Magnet . |
| 5,496,304 | 3/1996 | Chasan . |

FOREIGN PATENT DOCUMENTS 65858  7/1914  Australia .

*Primary Examiner*—Michael Peffley
*Attorney, Agent, or Firm*—Thorpe, North & Western, L.L.P.

[57] ABSTRACT

An apparatus and method are disclosed for marking the proper location of incisions to be made during a surgical procedure and for coloring the skin. The apparatus includes a pinwheel with a plurality of marking points extending therefrom for penetrating the outermost layer of the epidermis. A reservoir supplies a marking agent so that as the penetrating member penetrates the epidermis, marking agent is left within the epidermis, thereby leaving a dotted line which may be followed when making incisions during surgery. The method includes penetrating the outermost layer of the epidermis and leaving marking agent between the outermost layer of the epidermis and an innermost layer of the epidermis.

17 Claims, 1 Drawing Sheet

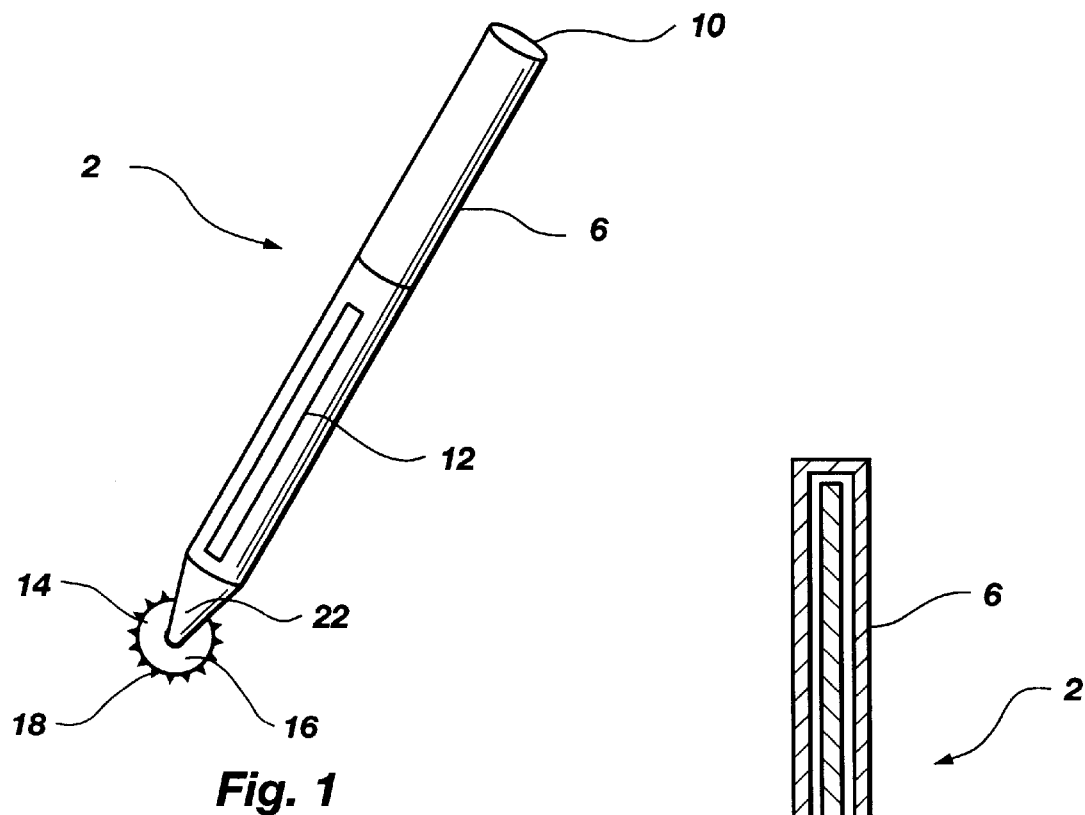
Fig. 1
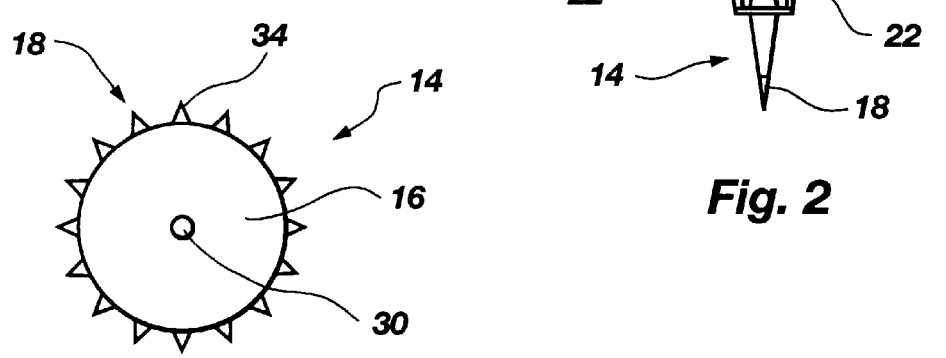
Fig. 2
Fig. 3

METHOD FOR COLORING THE SKIN

This application is a divisional of application Ser. No. 08/504,438, filed Jul. 20, 1995 now U.S. Pat. No. 5,713,890, which is a continuation-in-part of U.S. patent application Ser. No. 08/278,021 filed Jul. 20, 1994 now U.S. Pat. No. 5,496,304.

BACKGROUND OF THE INVENTION

The present invention relates to a marking pen, and in particular, to a marking pen which may be used during surgery so as to guide the surgeon in making a proper incision, and which may be used to otherwise mark the skin.

The use of marking pens during surgery is common. Often a surgeon will mark lines on a patient's body so as to know the proper place and length of the incision or incisions which will be made during the operation. Such lines can be particularly important in specialties such as plastic surgery where the operation is being conducted for cosmetic reasons. In such cases, it is extremely important that the incisions be at the proper location, and of the appropriate length. However, this is often difficult to do during surgery without the aid of markings.

Typically, a surgeon will use a felt tip pen to mark lines representing the desired incisions. Because of the patient's perspiration, natural oils and fluids that are used on the patient's body prior to surgery, such as antiseptic solutions, the lines made by the marking pens have a tendency to spread out or "bleed" after being drawn on the skin.

Additionally, once an incision has been made, blood usually spills on the patient's skin, causing additional blurring of the lines. While attempts have been made to form the marking portions of the pen in a fine tip, blood and other fluids cause the ink to spread, thereby obscuring the original lines.

Another problem with the marking pens of the prior art is that they have a tendency to dry out. Some pens dry out in the package and others dry out after a single use. The felt tip of the pen can also get "gummed up" with the betadine used on the patient. Because of these problems, many surgeons have been known to break open a pen and use the ink reservoir inside the pen to draw the lines. The reservoir, however, is fairly broad and results in a substandard marking.

Due to these problems with marking pens, some surgeons rely on primitive marking techniques. For example, some doctors will dip toothpicks or similar instruments in methylene blue. The toothpick, etc., is then dragged across the patient's skin to form a line. The toothpicks, however, will not hold a significant amount of the marking agent and must be repeatedly dipped when the surgeon is drawing a number of lines. Additionally, this method is slow and cumbersome.

In addition to the concerns with surgical marking pens, there are also many other instances in which a person may wish to place markings on the skin. For example, many women draw lines on each of their bottom eyelids with "eyeliner" so as to accentuate their eyes. While there have been proposals to permanently tattoo such marks, most consider this as generally undesirable, as the color of the eyeliner cannot be changed. Additionally, because the mark is permanent, is cannot be removed if the use of eyeliner becomes unfashionable.

To overcome these problems, there is a need for a marking pen which enables a user to make a line on the patient's skin which will not significantly broaden or smear. Additionally, the line made by the marking pen should be temporary so that it will disappear within a short period of time.

SUMMARY OF THE INVENTION

It is an object of the present invention to provide a marking pen which will produce a thin line on a patient's skin.

It is another object of the present invention to provide a marking pen which will produce lines which will not smear or blur when the skin becomes wet or oily.

It is another object of the present invention to provide such a pen which penetrates only the epidermis and will not penetrate the dermis during recommended use.

It is another object of the invention to provide such a pen which can color a portion of skin.

The above and other objects of the invention are achieved in a marking pen having a handle, and a fluid reservoir in fluid communication with a penetrating member, commonly referred to as a pinwheel. The pinwheel, for example has a plurality of marking points for puncturing at least one outer layer of the epidermis. As the pinwheel is rolled across a person's skin, the pinwheel leaves a temporary, tattooed line which may be used by the surgeon to make an accurate incision, or which may be used as eyeliner or some other body marking.

In accordance with one aspect of the invention, the pinwheel is less than 1.5 centimeters in diameter and the marking points extend therefrom are small, i.e. 3 millimeters or less and solid. The marking agent is disposed in the handle of the pen, such that a small amount of marking agent is left on the exterior of the marking point. As the pinwheel is rolled along a patient's skin, the small marking points deposit the marking agent as they penetrate the outermost layer of the epidermis, so as to form a dotted line on the patient's skin.

In accordance with another aspect of the invention, the marking pen can be repeatedly run over an area of skin, repeatedly adjusting the direction of the marking pen, so as to leave a plurality of colored marks in the epidermis so as to impart a color shade to the skin different from the natural color of the skin. By using different colors, the user can simulate conventional cosmetics, without fear that the coloration will leave if the skin becomes wet or oily.

BRIEF DESCRIPTION OF THE DRAWINGS

The above, and other objects, features and advantages of the invention, will become apparent from a consideration of the following detailed description presented in connection with the accompanying drawings, in which:

FIG. 1 shows a perspective view of a marking pen made in accordance with the present invention;

FIG. 2 shows a cross-sectional view of a preferred embodiment of the surgical marking pen of the present invention; and FIG. 3 shows a close-up view of the pinwheel of the present invention.

DETAILED DESCRIPTION

Reference will now be made to the drawings in which the various elements of the present invention will be given numeral designations and in which the invention will be discussed so as to enable one skilled in the art to make and use the invention. Referring to FIG. 1, there is shown a surgical marking pen, generally indicated at 2, for marking lines on a patient's body prior to, or during surgery. The marking pen 2 has a body 6 which is analogous to other marking pens in that the body contains a reservoir (not shown) for holding a supply of a marking agent, such as ink. The marking pen 2 may be disposable, or refillable through a cap, such as cap 10. Disposed in the side of the handle 6 may be a window 12 to enable a user to tell if the marking pen 2 is running out of marking agent. However, it is anticipated that a typical embodiment of the invention will use a felt reservoir mechanism to hold ink. Those familiar with such reservoirs will appreciate that it is often difficult to tell the amount of marking agent held simply by looking at the felt.

Attached to an end of the marking pen 2 is a pinwheel 14 which is formed from a central section 16 and a plurality of marking points 18 which extend from the central section. As will be explained in further detail below, the marking points 18 allow a patient to be marked with fine lines which do not blur or smudge during surgery. The marking points 18 of the pinwheel 14 can also be used to draw lines on the skin, as is commonly done when applying cosmetics, or to color the skin by repeated rolling the pinwheel over a defined area.

In a typical embodiment, the pinwheel 14 will be less than 1.5 centimeters in diameter, and the marking points 18 will be less than 3 millimeters in length. In a preferred embodiment of the invention, the pinwheel is less than 1 centimeter in overall diameter, and the marking points 18 extend less than 2 millimeters in length.

The small size of the pinwheel 14 offers several advantages. First, the small size limits the penetration of the marking points 18. As the pinwheel 14 is rolled across a person's skin with a moderate amount of pressure, the tapered marking points 18 will allow the tip to only penetrate a portion of the epidermis unless an significant amount of pressure is placed on the pinwheel 14. When a very small pinwheel 14 is used, only the most outer layers of the epidermis are penetrated. This allows the marking agent to be set in the skin sufficiently deep that it will not be interfered with by liquids on the skin's outer surface. However, by only penetrating the epidermis, the pinwheel will not cause bleeding caused by puncturing the dermis, and the pinwheel sets the marking agent sufficiently shallow that the marking agent will sluff off with the outer layers of the epidermis within a couple of days. Thus, it is not necessary to use a temporary dye, as the marking agent becomes inherently temporary.

The second major advantage of the small pinwheel 14 is the effect on the patient. While a large pinwheel of marking points will typically frighten a patient or other user, a pinwheel of the size described causes little fear, as the small pinwheel appears to be harmless. Furthermore, by penetrating only the outer layer of the epidermis, the person on whom the pinwheel 14 is used will not experience any pain.

A third major advantage of the small size of the pinwheel 14 of the present invention is the ease with which it may be turned from one direction to another. When drawing a line on human skin, several obstacles must be overcome. Not only must the user be concerned with making small radius turns, but the same must typically be made as the pinwheel is moving up and down along the uneven skin surface. By limiting the size of the pinwheel 14 to less than 1.5 centimeters, and preferably to less than 1 centimeter, the pinwheel may be easily turned around sharp corners and other irregular surfaces of the skin.

The pinwheel 14 is attached to the pen body 6 by a pair of arms 22. Typically, the pen body 6 is formed out of plastic, and the arms 22 and pinwheel 14 are formed from a metal such as aluminum or stainless steel. However, the arms 22 and even the pinwheel 14 could be formed from a durable plastic or some other similar material.

In addition to its use as a surgical marking pen, the marking pen 2 may also be useful for coloring the skin, as is typically done with cosmetics. For example, instead of using eyeliner that comes off during recreational activities, or permanently tattooing a line beneath the eyes, the marking pen 2 of the present invention could be used to apply a line on the eyelid below the eye. Unlike conventional cosmetics, the line will not bleed or come off when swimming or engaging in other recreational activities. However, unlike a permanent tattoo, the eyeliner will come off in a couple of days and a different color may be applied if desired.

In addition to using the marking pen to simulate eyeliner, the marking pen could also be used to imitate other conventional cosmetics. Instead of applying blush which may clog pores and come off during recreational activities, a marking pen 2 having a marking agent of the desired color could simply be rolled over the area to be colored several times until the desired shading is achieved. Within a couple of days, the color will disappear as the epidermal layers of skin are sloughed off.

Referring now to FIG. 2, there is shown a side cross-sectional view of the marking pen shown in FIG. 1. The marking pen, 2, includes the pen body 6 or handle and a reservoir mechanism 24 for holding a marking agent. Typically, the reservoir mechanism 24 will be a felt-like material, such as that used in "felt tipped" pens.

The pinwheel 14 is disposed at a bottom of the pen body 6 so that the marking points 18 which extend from the central section 16 of the pinwheel 14 contact the bottom of the reservoir mechanism 24 with each pass. Preferentially, a groove 28 is formed in the reservoir mechanism 24. The groove 28 is disposed so that the marking points 18 of the pinwheel 14 pass therethrough to readily pass the marking agent to the marking points 18 of the pinwheel 14 by direct contact without causing an excessive amount of friction.

As the marking points 18 pass next to the felt defining the sides of the groove 28, a small amount of marking agent is transferred to the end of the marking point. The marking agent is held in place by surface tension of the marking agent. As the respective marking points contact the skin, a small puncture is formed and the marking agent is deposited therein. As the pinwheel 14 is rolled along the skin, a plurality of marks are left so as to form a dotted line. If a permanent marking agent is used, the line will last as long as the layer of the epidermis in which it is deposited remains. Once the epidermal layer is sloughed off, the marking agent and the line will disappear.

If a person wished to use the marking pen for cosmetic reasons, an area of the skin could be colored by repeatedly running the pinwheel over the skin and changing the direction of the pinwheel slightly with each pass.

Referring now to FIG. 3, there is shown a close-up view of the pinwheel 14. The pinwheel 14 includes a center section 16 with a hole 30 disposed therethrough for attachment to the arms 22. The marking points 18 are disposed so that they have sufficient taper from the center section 16 to a point, such as point 34, so that penetration of the skin is limited to the tip of the respective marking point. The taper has several benefits. For example, by having the entire length of the marking points 18 tapered, the marking points 18 provide resistance to the point 34 entering more than a few cellular layers into the epidermis. Thus, unless considerable pressure is placed in the pinwheel 14, the point 34 will not enter the dermis. By limiting penetration of the point 34 to the epidermis, the marking points 18 prevent pain to the person on whom the marking pen is being used, and also prevent any permanent marks which might result from a permanent marking agent being deposited in the dermis. Thus, it is ideal if the length of the marking points 18 is 2 millimeters or less.

Another advantage of the taper is that promotes the proper transfer of the marking agent from the reservoir mechanism 24 (FIG.2) into the skin of the patient. If the taper were not provided, the transfer of marking agent would be less efficient and would result in occasional splattering of the marking agent.

Typically the outer surface of the marking points will be either planar or convex. If a concave portion is provided, there is an increased chance that the marking agent will bleed as the marking points enter the skin.

Thus there is disclosed a marking pen for coloring the skin. Those skilled in the art will recognize that numerous modifications may be made the embodiment disclosed without departing from the scope and spirit of the present invention. The appended claims are intended to cover such modifications.

I claim:

1. A method for temporarily tatooing a human body, the method comprising:
   (a) making a plurality of penetrations in a person's epidermis such that each of the penetrations extends to a position between an innermost layer and outermost layer of the epidermis;
   (b) depositing a temporary marking agent in each penetration so as to provide an image along the human body.

2. The method for temporarily tatooing a human body of claim 1, wherein the method comprises, more specifically, making the plurality of penetrations in the person's body at a desired location, so as to indicate the desired location at a later time.

3. The method for temporarily tatooing a human body of claim 2, wherein the desired location is the proper place for a surgical incision, and wherein the image comprises a dotted line.

4. The method for temporarily tatooing a human body of claim 1, wherein the method comprises, more specifically, making a plurality of perforations in the epidermis using a solid marking point, and using the solid marking point to deposit marking agent in said perforations.

5. The method for temporarily tatooing a human body of claim 4, wherein the method comprises, more specifically, rolling a pinwheel with a plurality of marking points extending radially outwardly therefrom over the epidermis.

6. A method for selectively coloring an area of human skin, the method comprising:
   (a) making a penetration into a person's epidermis such that the penetration extends to a position between an innermost layer of the epidermis and an outermost surface of the epidermis;
   (b) depositing a colored marking agent in the penetration; and
   (c) repeating steps (a) and (b) a sufficient number of times to as to color the area of skin to a desired color.

7. The method for selectively coloring an area of human skin of claim 6, wherein steps (a) and (b) comprise, more specifically, using a pinwheel with a plurality of marking points extending radially outward therefrom, each of the marking points having colored marking disposed thereon so as to deposit a colored marking agent into the epidermis when each marking point penetrates the outermost layer of the epidermis.

8. The method for selectively coloring an area of human skin of claim 7, wherein step (c) comprises rolling the pinwheel over the skin to form a plurality of colored dots on the skin.

9. The method for selectively coloring an area of human skin of claim 6, the method comprising, more specifically, making a penetration into a person's epidermis with a solid marking point to deposit marking agent between an outermost layer of the epidermis and the innermost layer of the epidermis.

10. The method for selectively coloring an area of human skin of claim 6, the method comprising, more specifically, depositing temporary marking agent in the epidermis such that the marking agent will disappear after a predetermined amount of time.

11. A method for marking the proper place for a surgical incision to be made on a patient's body, the method comprising:
   (a) making a plurality of penetrations in the patient's epidermis such that each penetration extends to a position between the innermost layer of the epidermis and the outermost surface of the epidermis; and
   (b) depositing a marking agent in each penetration so as to draw a dotted line along the patient's epidermis and mark the location of an incision to be made on the patient.

12. The method for marking the proper place for a surgical incision to be made of claim 11, wherein step (a) comprises, more specifically, making a plurality of perforations in the patient's epidermis such that each perforation extends slightly inward of the outermost surface of the epidermis.

13. The method for marking the proper place for a surgical incision to be made of claim 12, comprising the more specific step of using a solid marking point to make the perforations and to deposit the marking agent inward of the outermost layer of the epidermis.

14. The method for marking the proper place for a surgical incision to be made of claim 11, wherein step (b) comprises depositing a temporary marking agent such that the marking agent in the epidermis will disappear following surgery.

15. The method for marking the proper place for a surgical incision to be made of claim 11, wherein steps (a) and (b) comprise, more specifically, using a pinwheel with a plurality of marking points extending radially outward therefrom, each of the marking points having colored marking agent disposed thereon.

16. The method for marking the proper place for a surgical incision to be made of claim 15, wherein the method further comprises selecting a pinwheel having marking points which are configured to penetrate only to a position between an innermost layer and the outermost layer of the epidermis.

17. The method for marking the proper place for a surgical incision to be made of claim 15, wherein the method further comprises rolling the pinwheel over the epidermis.

* * * * *